(12) United States Patent
Azar et al.

(10) Patent No.: US 8,066,662 B2
(45) Date of Patent: Nov. 29, 2011

(54) INTRADERMAL NEEDLE-LESS INJECTION DEVICE

(76) Inventors: Zion Azar, Shoham (IL); Eyal Baror, Shoham (IL); Amikam Gershonovitz, Modi'in (IL); Pini Shalev, Herzeliya (IL); Gad Lev Konya, Neve Mivtach (IL); Yigal Ringart, Givaat Eela (IL)

( * ) Notice: Subject to any disclaimer, the term of this patent is extended or adjusted under 35 U.S.C. 154(b) by 0 days.

(21) Appl. No.: 12/890,727

(22) Filed: Sep. 27, 2010

(65) Prior Publication Data

US 2011/0015567 A1 Jan. 20, 2011

Related U.S. Application Data

(62) Division of application No. 12/306,690, filed on Dec. 25, 2008, now Pat. No. 7,824,360.

(60) Provisional application No. 60/816,866, filed on Jun. 28, 2006, provisional application No. 60/907,564, filed on Apr. 9, 2007.

(51) Int. Cl.
*A61M 31/00* (2006.01)
(52) U.S. Cl. ................ 604/70; 604/71; 604/73
(58) Field of Classification Search .............. 600/431, 600/433–435; 604/68–72, 151–155
See application file for complete search history.

(56) References Cited

U.S. PATENT DOCUMENTS

| 4,282,867 A * | 8/1981 | Du Toit .................. 601/161 |
| 5,569,190 A * | 10/1996 | D'Antonio ................ 604/72 |
| 2003/0088207 A1 | 5/2003 | Rogatchev et al. |
| 2005/0085767 A1* | 4/2005 | Menassa .................. 604/68 |
| 2008/0071218 A1* | 3/2008 | D'Antonio et al. ......... 604/152 |

FOREIGN PATENT DOCUMENTS

| WO | WO9817332 A2 | 6/1998 |
| WO | WO0189613 A1 | 11/2001 |
| WO | WO0249697 A1 | 6/2002 |

* cited by examiner

*Primary Examiner* — Nicholas D Lucchesi
*Assistant Examiner* — Gerald Landry, II

(57) ABSTRACT

A programmable injection device, comprising: a nozzle comprising a nozzle head with a fluid input hole and a distinct injection hole, the nozzle head accepts a dose of fluid from the fluid input hole to be injected into the skin of a patient through the injection hole, without use of a needle, a fluid capsule that is connected to said nozzle head and is adapted to provide the nozzle head with multiple doses of fluid for successive injections, without replacing the fluid capsule, an injection head that is adapted to have said fluid capsule and said nozzle head mounted onto it, comprising a first mechanism adapted to forcefully push a dose of a programmable amount of fluid from said fluid capsule to said nozzle head and a second mechanism for injecting by an programmable pressure said dose of fluid from said nozzle head into the skin of a patient in at least one of a programmable velocity or a programmable pressure applied to the skin surface.

19 Claims, 6 Drawing Sheets

INTRADERMAL NEEDLE-LESS INJECTION DEVICE

RELATED APPLICATIONS

The current application is a divisional application of U.S. application Ser. No. 12/306,690 filed Dec. 25, 2008, now U.S. Pat. No. 7,824,360 which claims priority from U.S. provisional applications No. 60/816,866 filed on Jun. 28, 2006 and application No. 60/907,564 filed on Apr. 9, 2007, the disclosures of which are incorporated herein by reference.

FIELD OF THE INVENTION

The present invention relates generally to needle-less injection of fluids subcutaneously or intradermally, and specifically to methods and devices for performing such.

BACKGROUND OF THE INVENTION

In many medical and cosmetic procedures there is a need to transfer fluids to areas below the surface of the skin, for example injecting insulin to diabetics and filling the dermal layer of the skin with collagens or other materials to preserve a youthful look. The most common method for introducing the fluids is by using a needle to inject the fluid to the desired position. The use of needles to administer the fluids requires that the administrator be trained to perform the procedure correctly so as not to cause damage. In many cases the exact position of injection is important to achieve the correct results. Generally, the use of needles causes damage to the skin and a significant amount of time is required for the damage to heal.

In recent years the injection of fluids using needle-less injectors has advanced. When using needle-less injectors, less training is required for a person to administer the injection, thus for example mass vaccination campaigns can be performed using untrained staff. Additionally, when using needle-less injections the penetration hole is generally smaller thus enabling the administration of more injections while minimizing damage to the surface of the skin. Additionally, newer skin augmentation methods rely on the self healing process of the skin, wherein the skin rejuvenates itself. In rejuvenation layers are thickened, and more collagen fibers are introduced. When using a needle damage is incurred to the skin surface but little trauma is caused to the cells of the internal layers of the skin, thus little rejuvenation is achieved.

A device that injects fluid subcutaneously or intradermally needs to be able to create a high pressurized jet of fluid with a small diameter so that it will be able to penetrate the epidermis layer of the skin. Generally, the device is more complicated than the common syringe for injecting fluids with a needle. Thus the needle-less injector tends to be heavier, more expensive and harder to control than the common needle injector.

Additionally, due to its simplicity and low cost the common needle injector is generally intended for a single use, thus preventing contamination and the spread of disease. In contrast the more complex needle-less device is mostly non-disposable and needs requires sterilization or additional precautions to prevent the transfer of contamination from one patient to another.

SUMMARY OF THE INVENTION

An aspect of an embodiment of the invention, relates to a needle-less injection device for injecting a fluid into the skin of a patient. The device includes a capsule for providing the fluid to the device. The capsule provides one or more doses of the fluid for injection into the skin of a patient. A nozzle is connected to the capsule (e.g. directly or with a tube) to receive a dose of fluid for injecting. The device includes an injection head to accommodate the capsule and the nozzle, wherein the injection head has a first mechanism to push a dose from the capsule into the nozzle head, and a second mechanism to inject a high pressure jet stream of the fluid into the skin of the patient. Optionally, a third mechanism is used to coordinate between the two mechanisms so that they will interact together. In an exemplary embodiment of the invention, the third mechanism positions the second mechanism according to the actions that need to be taken by the device. When a dose of fluid is loaded in the nozzle by the first mechanism the third mechanism places the second mechanism in a first position. When the fluid is loaded in the nozzle and ready for injection, the third mechanism places the second mechanism in position to inject the fluid. After injecting the fluid the third mechanism releases the second mechanism so that the process may be repeated.

In an exemplary embodiment of the invention, all of the mechanisms are activated by compressed gas. Optionally, a single source of compressed gas activates all mechanisms. In some embodiments of the invention, the mechanisms are activated by other methods, such as a spring or an electrical motor. In some embodiments of the invention, one mechanism is activated by one method and the other mechanisms are activated by a different method.

In some embodiments of the invention, the device includes a base for supporting the injection head so that a person does not need to support the weight of the device. Optionally, a beam is connected to and positioned above the device to support the injection head. In an exemplary embodiment of the invention, the beam is weighted at different points so that the injected head will be balanced by the beam. Alternatively, the beam is weighted so that the beam will lift the injection head when not being held by the user.

In an exemplary embodiment of the invention, the capsule provides a number of doses for treating a patient and can be replaced with a new capsule when its content is finished. Optionally, the nozzle and the connection between the nozzle and the capsule are also disposable. Optionally, the nozzle is replaced for each patient, since it might be in contact with the patient's skin and might be in contact with blood from the patient.

In some embodiments of the invention, a nozzle base is provided to interface between the nozzle and the patients skin so that a specific distance will be maintained when injecting fluid into the patients skin. Optionally, the nozzle base is adapted to confine a specific shaped area during injection so that the injected fluid will disperse mainly throughout the confined area. In an exemplary embodiment of the invention, a larger skin area is injected like in a tiling process by injecting an area and then injecting the neighbor areas to cover the larger area without overlapping.

There is thus provided according to an exemplary embodiment of the invention, a needle-less fluid injection device, comprising:

a nozzle head with an injection hole for accepting a dose of fluid to be injected into the skin of a patient;

a fluid capsule that is connected to the nozzle head and provides the nozzle head with one or more doses of fluid for injection;

an injection head for mounting the fluid capsule and the nozzle head comprising a first mechanism for releasing a dose of fluid from the fluid capsule to the nozzle and a second mechanism for injecting the dose of fluid from the nozzle into the skin of a patient. Optionally the device further comprises a third mechanism to coordinate between the first and second mechanism; wherein the third mechanism is adapted to control the positioning of the second mechanism.

In an exemplary embodiment of the invention, the device further comprises, a base for supporting the injection head, and a beam coupled to the base. Optionally, one or more weights are positioned on the beam so that the injection head is balanced by the beam above the base. Alternatively, one or more weights are positioned on said beam so that said injection head is lifted upward in equilibrium. In an exemplary embodiment of the invention, the device further comprises a compressor. Optionally, the device further comprises a gas balloon to store compressed gas. In an exemplary embodiment of the invention, the device further comprises a pressure control valve to regulate the pressure provided to the injection head. Optionally, the fluid capsule is disposable. In an exemplary embodiment of the invention, the nozzle is disposable. In an exemplary embodiment of the invention, the device further comprises a disposable tube to connect between the fluid capsule and the nozzle. Optionally, the second mechanism injects the fluid with an initial pressure of between 100 to 150 Atmospheres.

In an exemplary embodiment of the invention, the first mechanism is activated by a compressed gas. Alternatively, the first mechanism is activated by an electric, magnetic or electromagnetic force. Further alternatively, the first mechanism is activated by a spring. In an exemplary embodiment of the invention, the second mechanism is activated by a compressed gas. Alternatively, the second mechanism is activated by an electric, magnetic or electromagnetic force. Further alternatively, the second mechanism is activated by a spring. In an exemplary embodiment of the invention, the injection hole of the nozzle has a diameter of less than 0.5 mm. Optionally, the diameter of the injection hole of said nozzle is between 0.1 to 0.3 mm. In an exemplary embodiment of the invention, the nozzle has multiple injection holes. Optionally, the nozzle has an additional hole on the side to release air from the fluid before injecting the fluid. In an exemplary embodiment of the invention, the device is programmable. Optionally, the velocity of the injected fluid is programmable. In an exemplary embodiment of the invention, the depth of penetration is programmable. Optionally, the amount of fluid released in a single injection is programmable. In an exemplary embodiment of the invention, the pressure applied to the fluid is programmable. In an exemplary embodiment of the invention, the device further comprises a nozzle base for the nozzle head which positions the injection hole at a predetermined distance from the skin of the patient. Optionally, each side of the nozzle base is adapted to position the nozzle head at a different distance from the skin of the patient and the distance is selectable by rotation of the nozzle head. In an exemplary embodiment of the invention, the distance is between 1 to 20 mm. Optionally, the nozzle base is transparent and marked on the sides with a view finder to assist in positioning the nozzle base. In an exemplary embodiment of the invention, the nozzle base is adapted to confine a specific shaped area of skin during injection.

There is thus further provided according to an exemplary embodiment of the invention, a method of injecting fluid into skin, comprising:

pushing a single dose of fluid from a disposable capsule to an injection nozzle, using a first mechanism;

positioning a second mechanism to allow the dose of fluid to enter the injection nozzle;

moving the second mechanism to extract air from the nozzle and be ready to inject the fluid;

injecting the fluid in the nozzle by exerting a high pressure on the fluid with the second mechanism;

releasing the second mechanism to allow injection of another dose of fluid;

wherein coordination between the first mechanism and the position of the second mechanism is controlled by a third mechanism; and wherein all three mechanisms are encased in a single encasement.

BRIEF DESCRIPTION OF THE DRAWINGS

The present invention will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
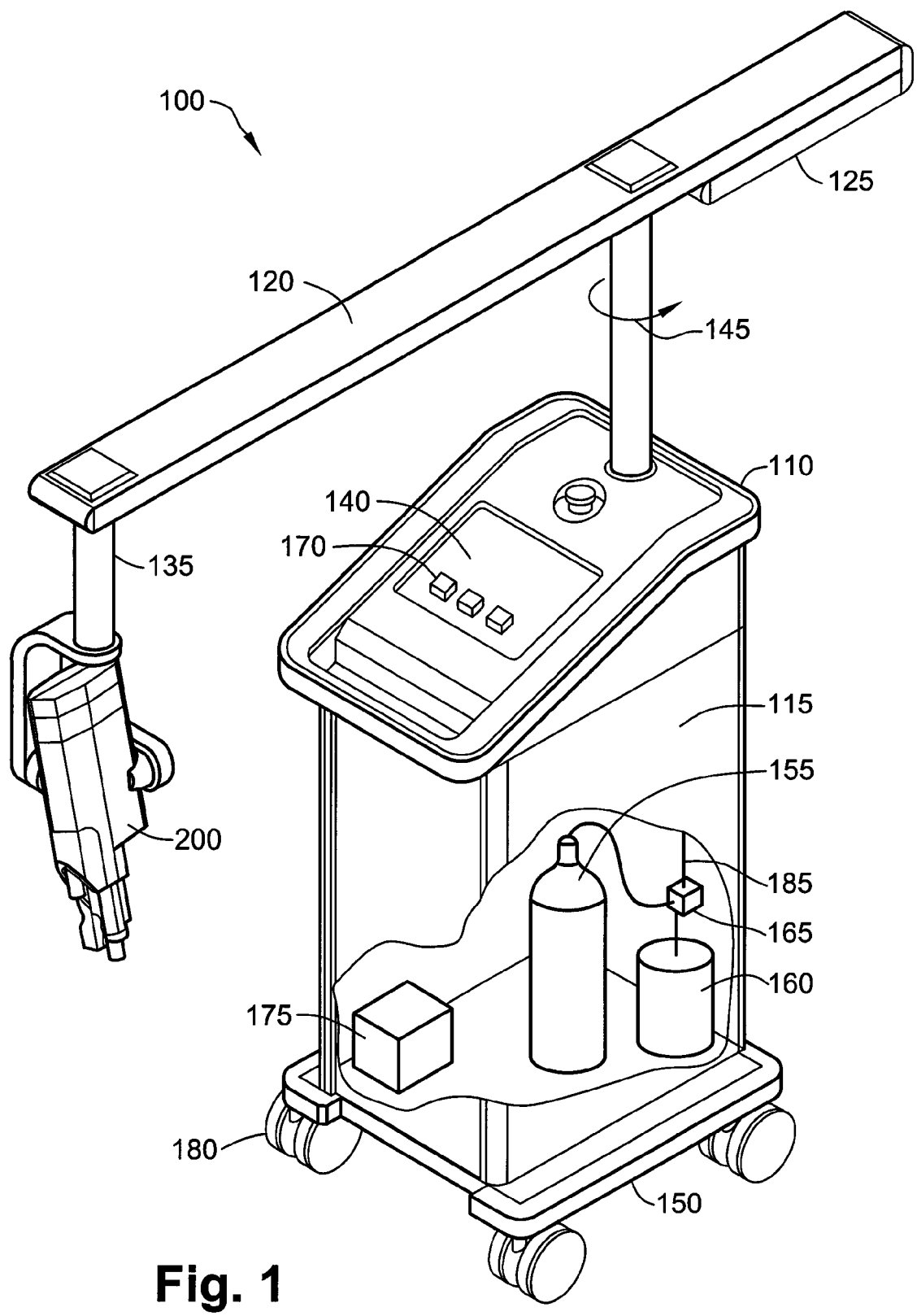
FIG. 1 is a perspective view of a needle-less injection device, according to an exemplary embodiment of the invention.

FIG. 1 is a perspective view of a needle-less injection device 100, according to an exemplary embodiment of the invention. In an exemplary embodiment of the invention, device 100 comprises an injection unit 200 for injecting fluids into the skin of a person or an animal. Injection unit 200 includes a mechanism for forming a highly pressurized jet stream of the fluid to penetrate the subject's skin. In some embodiments of the invention, the weight of injection unit 200 is greater than 100 gr, for example between 300 gr to 2 Kg and would be cumbersome for a person to hold and accurately aim at a patient without support. In an exemplary embodiment of the invention, injection unit 200 is supported by device 100, which comprises a crane system made up from a console 110, a vertical axis 145, a beam 120, a counter weight 125 and an pivot 135. Optionally, device 100 supports injection unit 200 in a balanced state so that the user only needs to provide a minimal force to position injection unit 200 and to hold it steady in contact with the patient. Alternatively, counter weight 125 is slightly heavier so that injection unit 200 will rise up and distance itself from the patient when not held by the user of device 100.

In an exemplary embodiment of the invention, the crane system allows injection unit 200 to be moved with little effort. Optionally, springs or hydraulic joints are used to control the motion of device 100 in multiple directions, so that injection unit 200 can be positioned for injection in the direction selected by the user with little effort.

In some embodiments of the invention, device 100 utilizes pressurized air or other gases to inject the fluid from injection unit 200, for example as shown in FIG. 1. Alternatively or additionally, the mechanism for injecting the fluid of injection unit 200 may be based on other mechanisms, for example a spring mechanism, which is loaded by the user and produces the highly pressurized jet stream of fluid when released. Another exemplary mechanism uses electromagnetic means (e.g. an electromagnetic motor) to push the fluid out of injection unit 200 at a high speed.

In an exemplary embodiment of the invention, console 110 includes a display 140 and input means 170, for example a touch screen, selection buttons or a keypad to communicate with the user and accept commands regarding the control of injection unit 200. Optionally, the user may define parameters such as:
1. Velocity of the jet injection;
2. Depth of penetration;
3. Amount of fluid released;
4. Pressure applied to the skin surface;
5. Pressure applied to the injected fluid;
6. Temperature of the injected fluid;
7. Time interval for application of the pressure;
8. Impulse shape.

Some of the above parameters may require the addition of extra parts to device 100, which are not provided in all embodiments of the invention, for example to control the temperature of the injected fluid injection unit 200 may require a temperature sensor and a heating or cooling element.

In an exemplary embodiment of the invention, console 110 serves as a weight to stabilize device 100. Optionally, console 110 additionally includes a closet 115 to accommodate a power supply 175, a gas balloon 155, a compressor 160 for compressing air and storing it in gas balloon 155, and a pressure control valve 165 to control the pressure provided by console 110. In an exemplary embodiment of the invention, device 100 includes cables 185 from console 110 to injection unit 200 (via vertical axis 145, beam 120 and pivot 135) to transfer the pressurized gas and/or electricity for controlling the device. Optionally, console 110 includes a base 150 with wheels 180 to allow device 100 to be readily moved near the patient. In some embodiments of the invention, base 150 includes weights or is made from a heavy material, for example lead or other heavy metals, to provide stability. In some embodiments of the invention, device 100 may weigh between 50 to 250 Kg although in some cases it may weigh more or less. Optionally, the height of device 100 is designed according to the height of a person, for example between 1.5 meters to 2 meters, so that it is readily applied to a sitting or standing person.

Figure 2A:
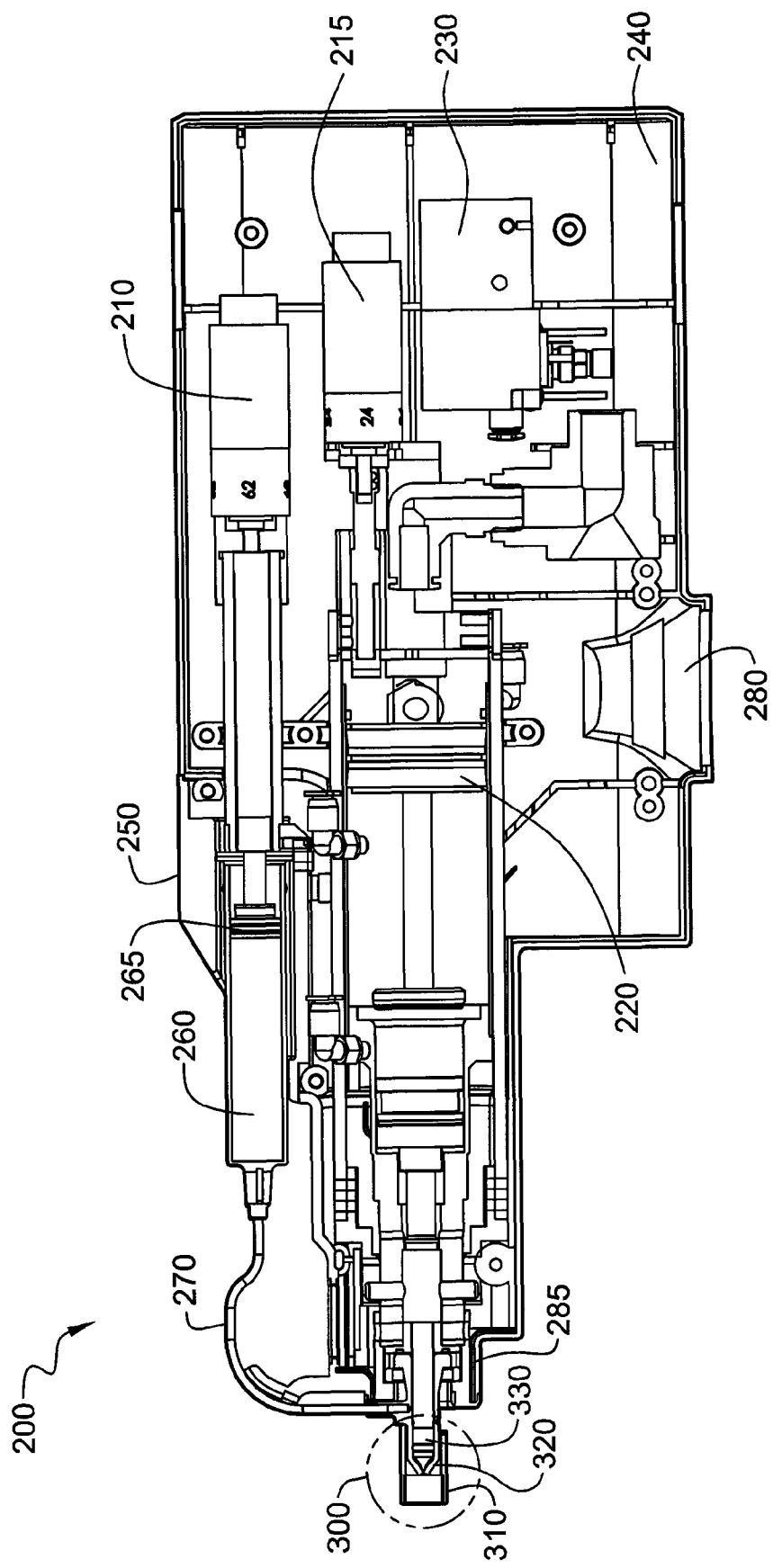
FIG. 2A is a cross sectional view of an injection unit from a needle-less injection device, according to an exemplary embodiment of the invention.
Figure 2B:
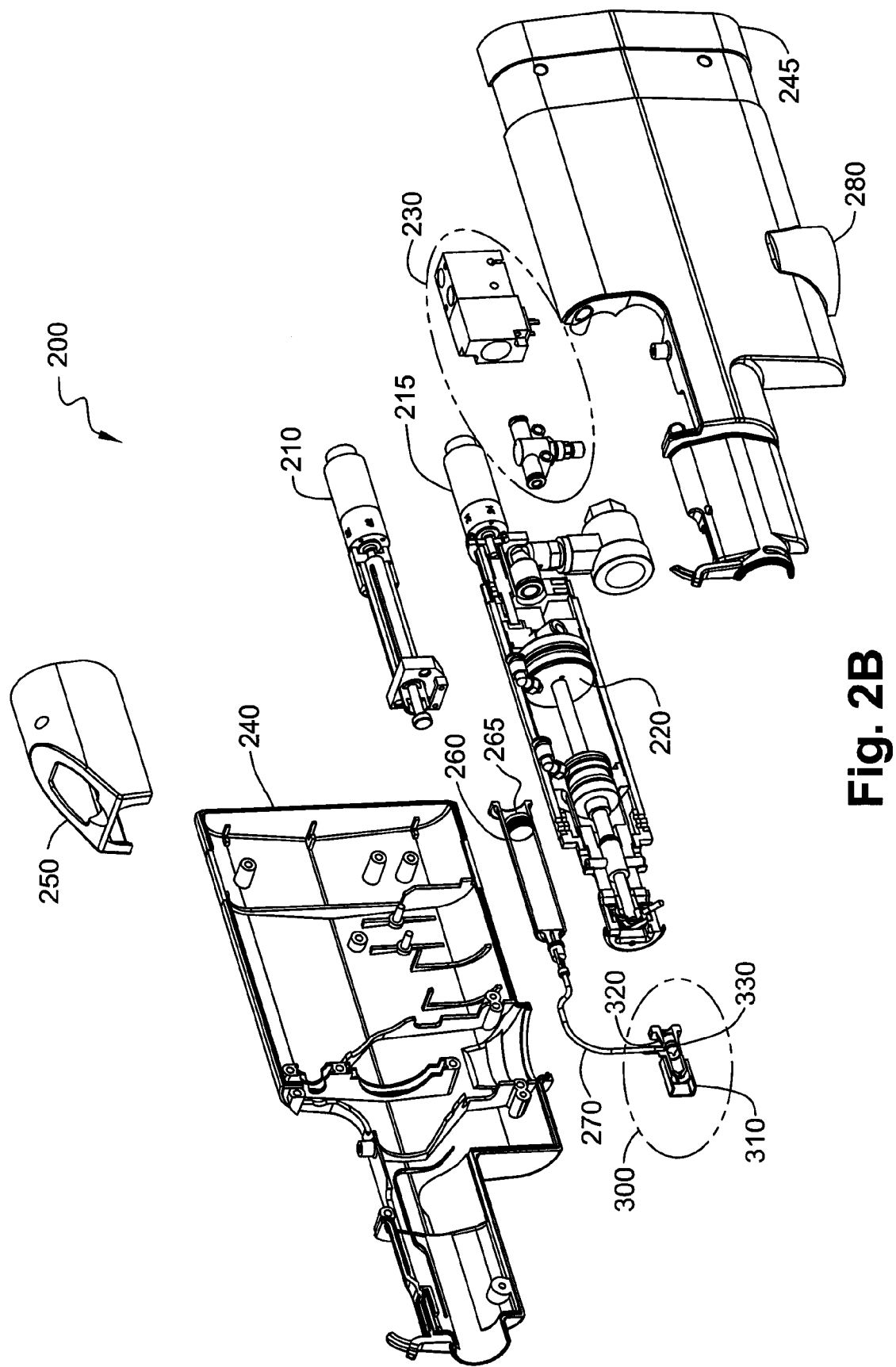
FIG. 2B is an exploded view of an injection unit from a needle-less injection device, according to an exemplary embodiment of the invention.

FIG. 2A is a cross sectional view of injection unit 200 from needle-less injection device 100, according to an exemplary embodiment of the invention, and FIG. 2B is an exploded view of injection unit 200 from needle-less injection device 100, according to an exemplary embodiment of the invention. In an exemplary embodiment of the invention, injection unit 200 is designed to accept a fluid capsule 260, which is provided with a quantity that is sufficient to provide a multiple number of injections, for example 50 injection doses or 100 injection doses. Optionally, a tube 270 is connected between fluid capsule 260 and a nozzle head 320 of a nozzle 300 to allow the transfer of a single dose of fluid for injection. In an exemplary embodiment of the invention, injection unit 200 comprises 3 mechanisms to be able to inject fluid into a patient. Optionally, a first mechanism 210 pushes a plunger that provides a single dose of fluid from fluid capsule 260 to nozzle 300. In an exemplary embodiment of the invention, a second mechanism 220 provides a high pressure force that injects the fluid from nozzle 300 into the patient. Optionally, a third mechanism 215 coordinates between the first mechanism and the second mechanism. In an exemplary embodiment of the invention, mechanism 215 positions mechanism 220 according to the stage of mechanism 210. Optionally, mechanism 215 positions mechanism 220 so that nozzle 300 is open to accept the fluid provided using mechanism 210. Then mechanism 215 positions mechanism 220 to be ready to inject the fluid. After injecting the fluid mechanism 215 releases mechanism 220 to accept another dose of fluid for injection In some embodiments of the invention, injection unit 200 only uses the first mechanism 210 and second mechanism 220, wherein the user positions the mechanisms so that the actions performed will be coordinated.

In some embodiments of the invention, a pressure control system 230 controls the provision of air pressure from gas balloon 155 to activate the three mechanisms (210, 215, 220). In an exemplary embodiment of the invention the above listed parts of injection unit 200 are placed in an encasement that comprises right panel 240, left panel 245 and fluid capsule protector 250. Optionally, injection unit 200 is attached to pivot 135 via pivot socket 280 so that it can be rotated by 180° or even 360° for positioning on a patient.

In an exemplary embodiment of the invention, fluid capsule 260 is sealed with a seal 265 (e.g. a rubber or plastic cork) to keep the fluid sterile. Optionally, seal 265 is placed internal to fluid capsule 260, so that it may be pushed inward by mechanism 210 to force the fluid from fluid capsule 260 into nozzle 300, without contaminating the fluid. In an exemplary embodiment of the invention, nozzle 300 is also sealed with a plunger 330 that is controlled by mechanism 220 to be raised and lowered in nozzle head 320, so that the fluid is injected without contact with injection unit 200. Optionally, the parts of injection unit 200 that provide the fluid and come in contact with the patient are all independent and disposable to prevent contamination and infection. Specifically, fluid capsule 260, tube 270, nozzle 300 and their subparts as listed above, are all disposable. In an exemplary embodiment of the invention, a new sterile fluid capsule 260, tube 270 and nozzle 300 are provided for injecting multiple doses of fluid for each patient. As an example in many cosmetic treatments a skin area is treated by performing multiple injections one after another while advancing incrementally across the skin to cover the entire area.

In some embodiments of the invention, capsule 260 and tube 270 may be provided for injection to multiple patients. Optionally, nozzle 300 is replaced for each patient and fluid capsule 260 is replaced when it is empty, for example when vaccinating a large number of people.

Figure 3A:
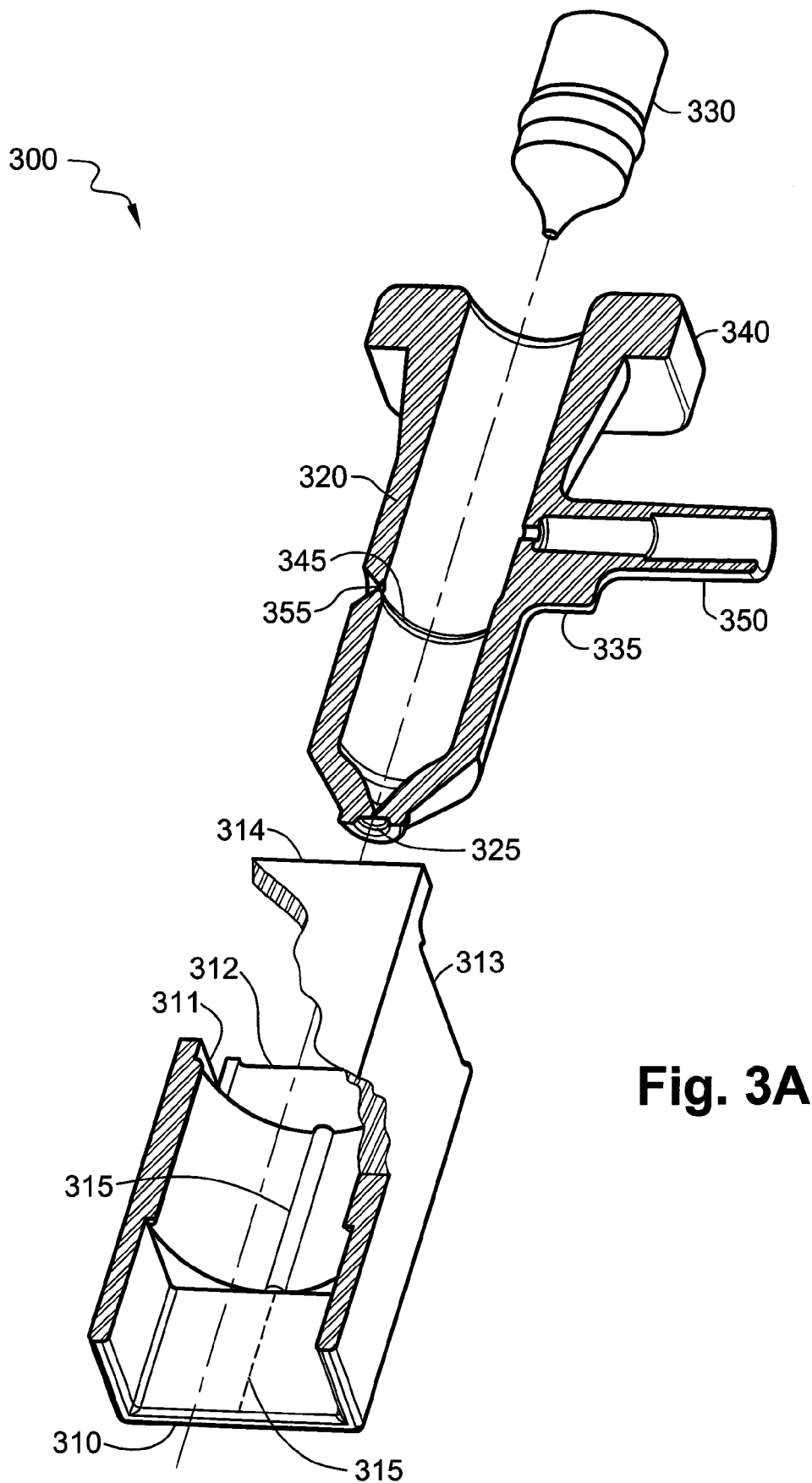
FIG. 3A is an exploded view of an injection nozzle, according to an exemplary embodiment of the invention.
Figure 3B:
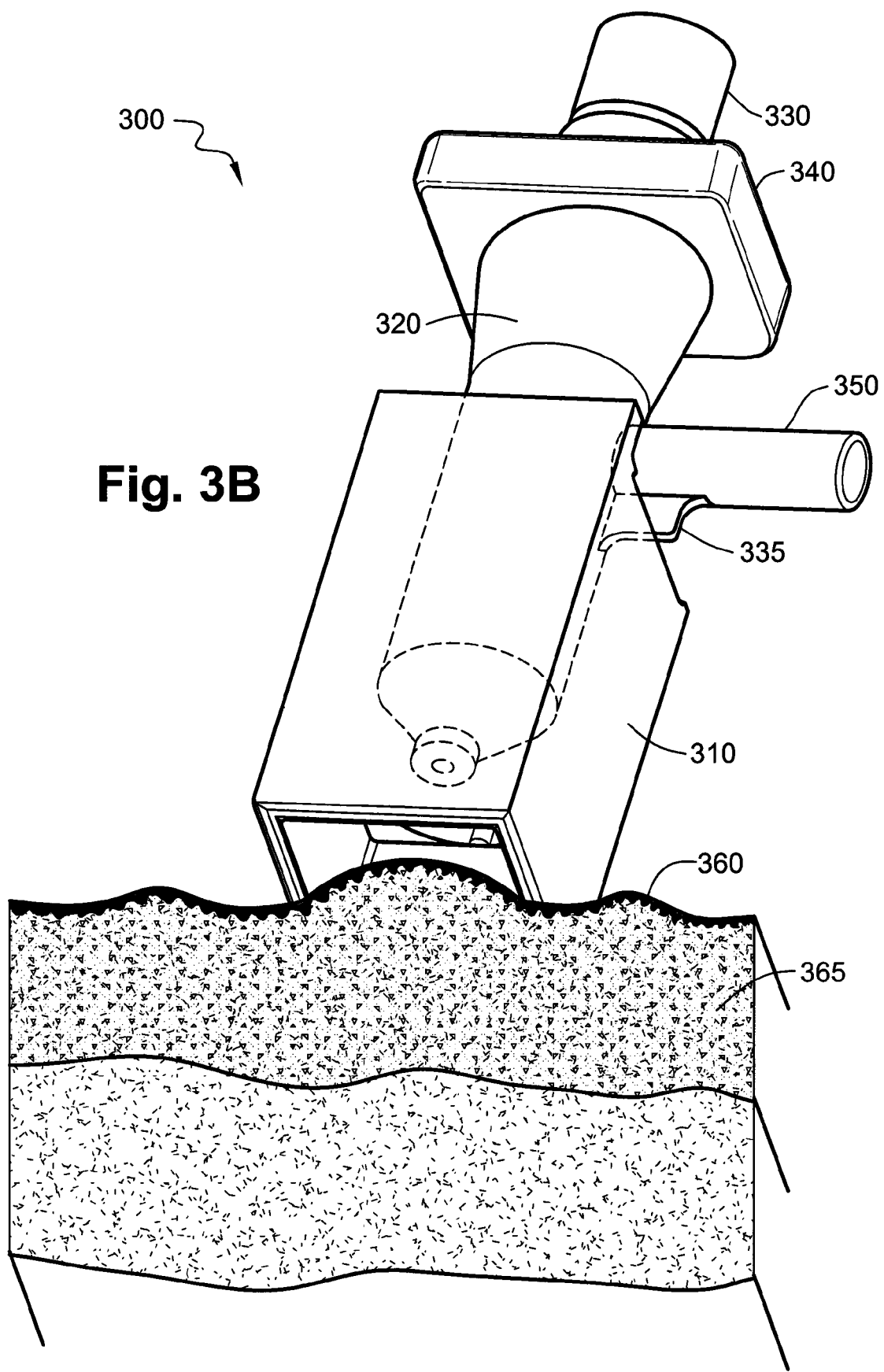
FIG. 3B is a schematic illustration of an injection nozzle in a deployed position, according to an exemplary embodiment of the invention.

FIG. 3A is an exploded view of injection nozzle 300, according to an exemplary embodiment of the invention, and FIG. 3B is a schematic illustration of injection nozzle 300 in a deployed position, according to an exemplary embodiment of the invention.

Optionally, as described above, nozzle 300 includes three separate parts, nozzle base 310, nozzle head 320 and a plunger 330. Nozzle head 320 is attached to injection unit 200 with nozzle interface 340, and plunger 330 is grasped by mechanism 220, so that it can be moved up and down in nozzle head 320. In an exemplary embodiment of the invention, nozzle head 320 comprises an entrance 350, which is attached to one end of tube 270 and receives a dose of the fluid for injection from fluid capsule 260. Optionally, the fluid fills up the lower part of nozzle head 320 according to the designated dosage (e.g. up to line 345 that is below entrance 350). Optionally, a pressure hole 355 is positioned on a side of nozzle head 320 above line 345 to allow air to exit when positioning plunger 330 and mechanism 220 in position for injecting the fluid from nozzle head 320.

In an exemplary embodiment of the invention, the fluid is ejected from nozzle head 320 via a small hole 325. Optionally, hole 325 is large enough to allow a jet stream of the fluid to be ejected through hole 325, but small enough (e.g. less than 0.5 mm) to prevent the fluid from dripping out when no pressure is exerted as a result of the viscosity of the fluid. Optionally, the size used for hole 325 depends on the type of fluid injected, for example for water a diameter between 0.1 mm and 0.3 mm is sufficient. In some embodiments of the invention, nozzle head 320 has multiple holes 325 to form multiple jet streams when injecting the fluid.

In some embodiments of the invention, nozzle base 310 may be provided with any shaped opening facing downward to be deployed on the patients skin and causing nozzle head 320 to be positioned at a preset distance from the patient's skin (e.g. between 1 mm to 20 mm). Optionally, when releasing mechanism 220 nozzle base 310 confines a patch of skin and pushes against the skin causing the confined area to rise toward nozzle head 320. As a result the injected stream disperses more evenly in the dermis below the confined area.

In an exemplary embodiment of the invention, the internal diameter of nozzle base 310 approximately matches the external diameter of nozzle head 320 so that nozzle head 320 will be held firmly by nozzle base 310. Optionally, the downward opening of nozzle base 310 may be rectangular or square to simplify the process of injecting fluid to a larger area of the patient's skin without overlap. Optionally, a user would inject the fluid to one position and advance incrementally over the skin until covering the entire larger area with or without overlap. In an exemplary embodiment of the invention, nozzle base 310 has a different height on different sides of its circumference, for example as illustrated in FIG. 3A side 314 is highest then side 313 then side 312 and then side 311. Optionally, nozzle head 320 comprises a rest protrusion 335, which is positioned to rest on one of the sides (311, 312, 313, and 314) of nozzle base 310 to prevent it from descending deeper into base 310 and getting closer to the skin of the patient. Thus by selecting a side for rest protrusion 335 the user determines the distance between hole 325 and the patient's skin, for example the distance may be set to be between 1 mm to 20 mm or more or less. Optionally, the distance between hole 325 and the patient's skin affects the form of the injection stream that penetrates the patient's skin.

Figure 4:
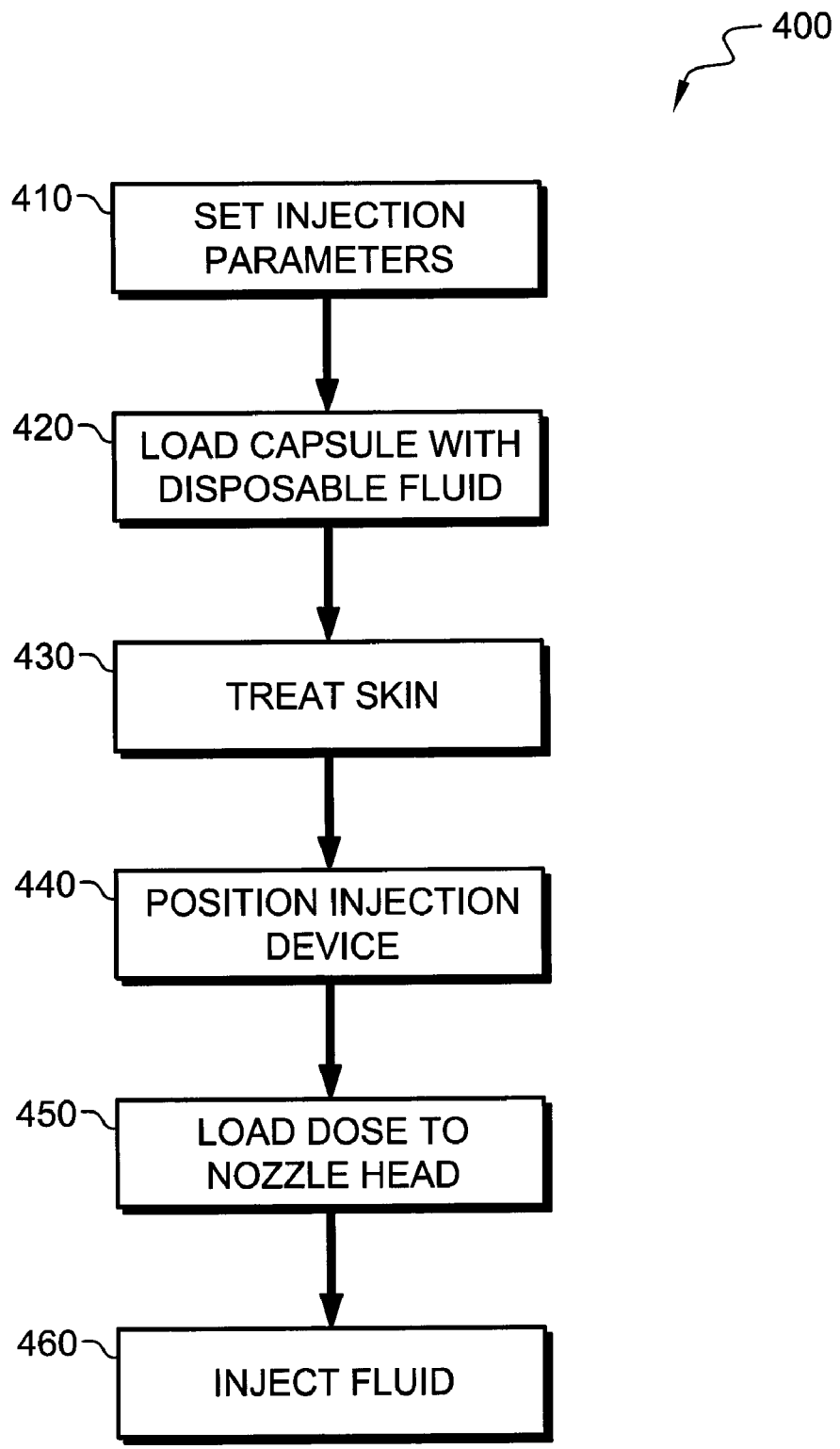
FIG. 4 is a flow diagram of a method of using a needle-less injection device, according to an exemplary embodiment of the invention.

FIG. 4 is a flow diagram 400 of a method of using needleless injection device 100, according to an exemplary embodiment of the invention. In an exemplary embodiment of the invention, a user programs device 100 setting (410) parameters for performing fluid injection, for example setting the pressure value that will be applied to inject the liquid or the size of the dose that will be injected each time. The user then loads (420) a fluid capsule 260 with the fluid that is to be injected. It should be noted that the fluid may be a gas, a liquid, a cream or a powder that was dissolved in liquid.

In an exemplary embodiment of the invention, the external layer of the skin is treated (430) prior to injecting the fluid, for example by applying lotions or moister (e.g. alcohol) to the injection area on the epidermis layer 360 of the patient's skin (shown in FIG. 3B) or by cooling or warming the area. Optionally, treatment of the skin can reduce resistance, reduce sensation or prevent contamination. In some embodiments of the invention, the patient's skin is treated for an extended amount of time (e.g. 40-60 minutes) prior to injection so that the injection process will be more effective.

After optionally treating the skin, injection unit 200 is positioned (440) over the area that needs to be injected. Nozzle base 310 is pressed against epidermis layer 360 causing the dermis layer 365 that is confined by nozzle base 310 to rise up toward nozzle head 320. In an exemplary embodiment of the invention the user of device 100 instructs injection head 200 to load (450) a dose of fluid into nozzle head 320, then injection head 200 releases mechanism 220 to apply pressure on the fluid in nozzle head 200 and inject it (460) in the form of a jet stream toward the patient's epidermis. In an exemplary embodiment of the invention, the jet stream is injected at a pressure between 100 Atmospheres to 200 Atmospheres, for example 120 Atmospheres or 150 Atmospheres, so that it will penetrate epidermis 360 and disperse in dermis 365. Optionally, control of the injection pressure determines the depth in the skin into which the injected fluid will reach.

It should be noted that the above process may be performed in a different order, for example treating the skin (430), loading the capsule (420), setting parameters (410), loading a dose (450), positioning the device (440) and then injecting (460) the fluid.

In some embodiments of the invention, nozzle base 310 is transparent and marked on the sides with a view finder 315 to assist in positioning nozzle base 310 on the patient's skin, for example the view finder may be marked at the median between the corners.

In some embodiments of the invention, injection unit 200 includes a sensor 285, which tests the quality of the skin being injected, for example using an ultrasound wave or a light. Optionally, parameters of device 100 are set automatically, according to the determined skin quality, for example using a higher injection pressure for hard skin and a lower injection pressure for soft skin.

In an exemplary embodiment of the invention, device 100 is used to inject a dermal filler fluid into aged skin to improve the cosmetic look of the skin. In the aging process the connections between the cells in the dermal layer are weakened causing the skin to become lax, wrinkled and dry. Optionally, by injecting a dermal filler material in a high speed stream the filler material penetrates epidermis 360 and disperses in dermis 365. When dispersing in dermis 365 the particles of the high speed stream traumatize the dermal cells initiating a healing process, which causes the dermal cells to be rejuvenated. The rejuvenation returns the youthful look and feel of the skin for an extended period (e.g. a few years). Immediately after injection, the dermal filler material provides the youthful look. Over time the dermal filler decomposes (e.g. within 1-3 months). At the same time the rejuvenation process begins to show so that in the long run the skin retains its youthful look. In an exemplary embodiment of the invention, the success of the cosmetic process is enhanced by using device 100. Optionally, by confining an area of the skin with nozzle base 310, when injecting the high speed stream of filler material, the filler material disperses better in the confined area. Thus by covering a larger skin area piece by piece a larger skin area can be covered more effectively.

In an exemplary embodiment of the invention, dermal filler fluids may include: collagen, hyaluronic acid, fat, silicon, water, Polymethylmethacrylate Microspheres (PMMA), Calcium Hydroxy Apatite Microspheres (CaHA), Polyvinyl Alcohol (PVA), Polyethylene Glycol (PEG) and the like. Optionally, the dermal filler material may be heated (e.g. to between 40° C.-70° C.) prior to injection, to enhance dispersion in the dermal layer.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the invention. Further combinations of the above features are also considered to be within the scope of some embodiments of the invention.

It will be appreciated by persons skilled in the art that the present invention is not limited to what has been particularly shown and described hereinabove. Rather the scope of the present invention is defined only by the claims, which follow.

The invention claimed is:

1. A programmable needle-less injection device, comprising:
   a nozzle comprising a nozzle head with a fluid input hole and an injection hole, the nozzle head accepts a dose of a fluid from the fluid input hole to be injected into skin of a patient through the injection hole, without penetrating the skin with a needle;
   a fluid capsule that is connected to said nozzle head; wherein said fluid capsule provides the nozzle head with multiple doses of fluid for successive injections, without replacing the fluid capsule;
   an injection head for mounting said fluid capsule and said nozzle head onto it, comprising a first mechanism adapted to forcefully push the dose of a programmable amount of fluid from said fluid capsule to said nozzle head and a second mechanism for injecting by a programmable pressure the dose from said nozzle head into the skin of the patient in at least one of a programmable velocity or the programmable pressure applied to a surface of the skin of the patient;
   wherein said nozzle head and said fluid capsule being independent from said injection head and being disposable; and
   wherein the disposable nozzle head includes a plunger that seals between the nozzle head and the second mechanism; and
   wherein the plunger is adapted to be moved up and down by the second mechanism to enable reception of multiple doses of fluid into the nozzle head and to inject them through the injection hole by the plunger.

2. The programmable injection device according to claim 1, wherein the programmable injection device is programmable for a depth of penetration of the fluid into the skin of the patient.

3. The programmable injection device according to claim 1, wherein the programmable pressure is controlled to determine a depth of penetration of the fluid into the skin of the patient.

4. The programmable injection device according to claim 1, wherein the programmable pressure is programmable in a range between 100 Atm and 200 Atm.

5. The programmable injection device according to claim 1, wherein the programmable pressure is programmable initially in a range between 100 Atm and 150 Atm.

6. The programmable injection device according to claim 1, wherein the programmable pressure is 120 Atm.

7. The programmable injection device according to claim 1, wherein the programmable pressure is 150 Atm.

8. The programmable injection device according to claim 1, wherein the programmable pressure is applied for a programmable time interval.

9. The programmable injection device according to claim 1, wherein the programmable pressure is applied in a programmable impulse shape.

10. The programmable injection device according to claim 1, wherein the programmable pressure is applied by a spring.

11. The programmable injection device according to claim 1, wherein a temperature of the fluid is programmable.

12. The programmable injection device according to claim 1, wherein the injection hole has a diameter of less than 0.5 mm.

13. The programmable injection device according to claim 1, wherein the injection hole has a diameter between 0.1 mm to 0.3 mm.

14. The programmable injection device according to claim 1, wherein the injection hole has a diameter that is determined by viscosity of the fluid.

15. The programmable injection device according to claim 1, wherein p between the injection hole and the skin of the patient is either more or less than 20 mm.

16. The programmable injection device according to claim 1, wherein a distance between the injection hole and the skin of the patient is between 1 mm to 20 mm.

17. The programmable injection device according to claim 1, further comprising a tube connecting between the fluid capsule and the nozzle.

18. The programmable injection device according to claim 17, wherein the tube is disposable.

19. The programmable injection device according to claim 1, wherein the fluid comprises at least one of collagen, hyaluronic acid, fat, silicon, water, Polymethylmethacrylate Microspheres, Calcium Hydroxy Apatite Microspheres, Polyvinyl Alcohol or Polyethylene Glycol.

* * * * *